US006921409B2

(12) United States Patent
Richard

(10) Patent No.: US 6,921,409 B2
(45) Date of Patent: Jul. 26, 2005

(54) TONGUE CLEANING DEVICE

(76) Inventor: James R. Richard, 20 Woodland Dr., Canton, CT (US) 06019

( * ) Notice: Subject to any disclaimer, the term of this patent is extended or adjusted under 35 U.S.C. 154(b) by 0 days.

(21) Appl. No.: 09/853,104

(22) Filed: May 10, 2001

(65) Prior Publication Data

US 2001/0041903 A1 Nov. 15, 2001

Related U.S. Application Data

(60) Provisional application No. 60/203,373, filed on May 10, 2000.

(51) Int. Cl.$^7$ .............................................. A61B 17/24
(52) U.S. Cl. ..................................................... 606/161
(58) Field of Search ................................ 606/161, 162, 606/160; 15/111, 110; 433/141; 132/308, 311; D24/147

(56) References Cited

U.S. PATENT DOCUMENTS

| | | | | |
|---|---|---|---|---|
| 1,179,426 A | * | 4/1916 | Hamilton .................... 606/161 |
| 1,200,596 A | * | 10/1916 | Daly ............................ 15/227 |
| 1,851,396 A | * | 3/1932 | Mabry ........................ 606/161 |
| 1,891,864 A | * | 12/1932 | Barrett ....................... 606/161 |
| 2,075,681 A | * | 3/1937 | Logue ........................... 401/7 |
| 2,491,274 A | * | 12/1949 | McNeill ........................ 604/1 |
| 3,070,102 A | * | 12/1962 | MacDonald ................. 132/84 |
| 3,298,507 A | * | 1/1967 | Micciche ...................... 206/46 |
| 3,943,592 A | | 3/1976 | Bhaskar et al. |
| 4,079,478 A | * | 3/1978 | Andrews, Sr. ............. 15/210.1 |
| 4,628,949 A | * | 12/1986 | Mas et al. ................... 132/308 |
| D290,426 S | * | 6/1987 | Courney ...................... D4/103 |
| 4,679,274 A | * | 7/1987 | Friedman ................... 15/167.1 |
| D332,352 S | * | 1/1993 | Caldwell et al. ............. D4/104 |
| 5,356,005 A | * | 10/1994 | Burrello ................... 206/362.4 |
| 5,613,262 A | * | 3/1997 | Choy-Maldonado ......... 15/160 |
| 5,678,273 A | * | 10/1997 | Porcelli .................... 15/104.94 |
| 5,735,864 A | * | 4/1998 | Heisinger, Jr. .............. 606/161 |
| 5,765,252 A | * | 6/1998 | Carr ......................... 15/104.94 |
| 5,817,114 A | | 10/1998 | Anderson et al. |
| 5,875,513 A | * | 3/1999 | Reinold ........................ 15/227 |
| 5,910,151 A | * | 6/1999 | Adedokun ................... 606/161 |
| 5,938,673 A | | 8/1999 | DePierro et al. |
| 5,951,578 A | * | 9/1999 | Jensen ........................ 606/161 |
| 5,967,152 A | | 10/1999 | Rimkus |
| 6,015,293 A | | 1/2000 | Rimkus |
| D427,310 S | * | 6/2000 | Haneiph .................... D24/147 |
| 6,112,356 A | * | 9/2000 | Hashey .................... 15/104.94 |
| 6,116,252 A | * | 9/2000 | Stelmach .................... 132/309 |
| 6,132,445 A | * | 10/2000 | Pavanelli .................... 606/161 |
| 6,352,545 B1 | * | 3/2002 | Wagner ...................... 606/161 |
| 6,383,202 B1 | * | 5/2002 | Rosenblood et al. ........ 606/161 |

* cited by examiner

Primary Examiner—Alissa L. Hoey
(74) Attorney, Agent, or Firm—St. Onge Steward Johnston & Reens LLC

(57) ABSTRACT

A tongue cleaning device having an elongated planar member integrally formed of a flexible material and defining a handle portion and a head portion. The head portion is adapted to be pressed with the tongue against a top surface of a user's mouth to conform the head portion to the shape thereof. The cleaning portion includes a first layer and a second layer where the first layer is the head portion of the elongated member and the second layer is backing material. The cleaning portion includes a plurality of cleaning projections protruding outwardly from the second layer. The handle potion is made of deformable material for deforming around a user's teeth and has periphery sized and shaped to fit within a roof of the user's mouth.

12 Claims, 1 Drawing Sheet

TONGUE CLEANING DEVICE

RELATED APPLICATIONS

This application claims the benefit of, under 35 U.S.C. §119(e) of U.S. Provisional Patent Application No. 60/203,373, filed May 10, 2000.

FIELD OF THE INVENTION

The present invention relates to an oral hygiene device, and more particularly to a device for cleaning and disinfecting the tongue.

BACKGROUND OF THE INVENTION

Generally, brushing, flossing and rinsing with mouthwash have been standard methods utilized to eliminate oral bacteria and bad breath. According to studies, however, bacteria on the surface of the tongue can cause up to 75% of bad breath odor. As such, numerous devices have been conceived to try to remove bacterial growth on the surface of the tongue, none of which has been particularly effective.

U.S. Pat. No. 5,817,114 to Anderson et al. discloses a tongue cleaner which includes a support member pre-shaped to fit snugly within the roof area of a user's mouth. Rather than the tongue cleaner having a periphery which fits within the roof of a user's mouth, the device disclosed in Anderson et al. includes recesses for receiving a user's teeth or, if the user has no teeth, a user's gums.

The tongue cleaner disclosed in Anderson et al. suffers from a number of disadvantages. As can be appreciated from the drawings, the device is relatively complex, costly to manufacture, and therefore not conducive to disposable use. In addition, the pre-shaped nature of the support member and the recesses for receiving a user's teeth or gums would require more than one universal style and size which could be used by all users. At the very least, one style is required for those having teeth and another for those without teeth. Moreover, although the Anderson et al. reference specifically attempts to provide a device which avoids causing a user to gag during tongue cleaning, the large size of the disclosed device may indeed lead to gagging in many users.

U.S. Pat. Nos. 5,967,152 and 6,015,293 to Rimkus disclose a tongue cleaning apparatus including an elongated handle having a solution storage cavity therein, an attachment utensil partially stored in the cavity, and a head component. The head component includes cleaning surfaces which may take the form of a plurality of hooks such as those found on the hook side of Velcro® hook and loop fasteners (FIG. 1) or a plurality of loops such as those found on the loop side of Velcro® hook and loop fasteners (FIG. 5).

Like the tongue cleaner disclosed in Anderson et al., the tongue cleaning apparatus disclosed in the Rimkus patents suffers from a number of disadvantages. One of such disadvantages is that the head component is rigid and relatively large, and is therefore uncomfortable and may promote gagging. Another disadvantage is that, although the Rimkus patents state that the cleaning apparatus disclosed therein is disposable, the apparatus is extremely complex, expensive to produce, and not readily disposable. Even the head portion, which is detachable from the rest of the apparatus, is complex and would not be readily disposable.

U.S. Pat. No. 3,943,592 to Bhaskar et al. and U.S. Pat. No. 5,938,673 to DePierro et al. both disclose tongue cleaning devices which include a flat, elongated member, such as a tongue depressor. Although the members may be bent at some location along their lengths, they are otherwise rigidly formed from wood or a molded plastic. The Bhaskar et al. device includes a brush portion comprised of hooks such as those found on the hook side of Velcro® hook and loop fasteners. The DePierro et al. device includes a brush portion made up of a plurality of flexible multifilament yarn bundles which form a loop pile.

The tongue cleaning devices disclosed in the Bhaskar et al. and DePierro et al. patents suffer from a number of disadvantages. One of such disadvantages is that the head component is rigid and cannot be contoured to the roof of the user's mouth. Such devices require the user to protrude his or her tongue and then brush the device over the tongue. This action will typically elicit a gagging reflex in a large number of users. Moreover, because the device does not conform to the user's tongue during use, pressure is not evenly distributed across the tongue, and cleaning may not evenly occur at all desired locations.

What is desired, therefore, is a tongue cleaning device which is relatively small and has a periphery which fits within the roof of a user's mouth, which is relatively simple in design and not costly to manufacture, and therefore conducive to disposable use, which may be used by a number of users having varying mouth sizes, which is flexible and can be contoured to the roof of the user's mouth, which can be contoured to the user's tongue during use, thus evenly distributing pressure across the tongue and promoting even cleaning at all desired tongue locations, and which avoids causing a user to gag during tongue cleaning.

SUMMARY OF THE INVENTION

Accordingly, it is an object of the present invention to provide a tongue cleaning device which is relatively small and has a periphery which fits within the roof of a user's mouth.

Another object of the present invention is to provide a tongue cleaning device having the above characteristics and which is relatively simple in design and not costly to manufacture, and therefore conducive to disposable use.

A further object of the present invention is to provide a tongue cleaning device having the above characteristics and which may be used by a number of users having varying mouth sizes.

Still another object of the present invention is to provide a tongue cleaning device having the above characteristics and which is flexible and can be contoured to the roof of the user's mouth.

Yet a further object of the present invention is to provide a tongue cleaning device having the above characteristics and which can be contoured to the user's tongue during use, thus evenly distributing pressure across the tongue and promoting even cleaning at all desired tongue locations.

Still yet a further object of the present invention is to provide a tongue cleaning device having the above characteristics and which avoids causing a user to gag during tongue cleaning.

These and other objects of the present invention are achieved by provision of a tongue cleaning device having an elongated planar member integrally formed of a flexible material and defining a handle portion and a head portion. The head portion is adapted to be pressed with the tongue against a top surface of a user's mouth to conform the head portion to the shape thereof. The cleaning portion includes a first layer and a second layer where the first layer is the head portion of the elongated member and the second layer is backing material. The cleaning portion includes a plurality of cleaning projections protruding outwardly from the second layer. The handle potion is made of deformable material for deforming around a user's teeth and has periphery sized and shaped to fit within a roof of the user's mouth.

Preferably, the elongated member is integrally formed of a thin, flexible plastic material. It is also preferable that the cleaning portion includes a backing material having an adhesive on a first surface thereof adhered to the head portion of the elongated member, and having a plurality of projections protruding from a second surface thereof. Preferably, the plurality of projections comprise a plurality of fiber loops. Most preferably, the cleaning portion comprises a loop portion of a hook-and-loop fastening system.

An antiseptic or antimicrobial compound may be carried in the cleaning portion of the tongue cleaning device. Preferably, the head portion of the elongated member is wider than the handle portion of the elongated member.

The invention and its particular features and advantages will become more apparent from the following detailed description considered with reference to the accompanying drawings.

DETAILED DESCRIPTION OF THE INVENTION

Figure 1:
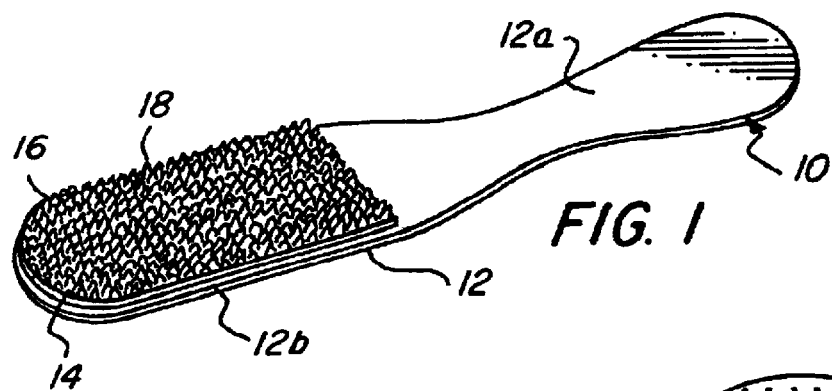
FIG. 1 is a perspective view showing an embodiment of a tongue cleaning device in accordance with the present invention.
Figure 2:
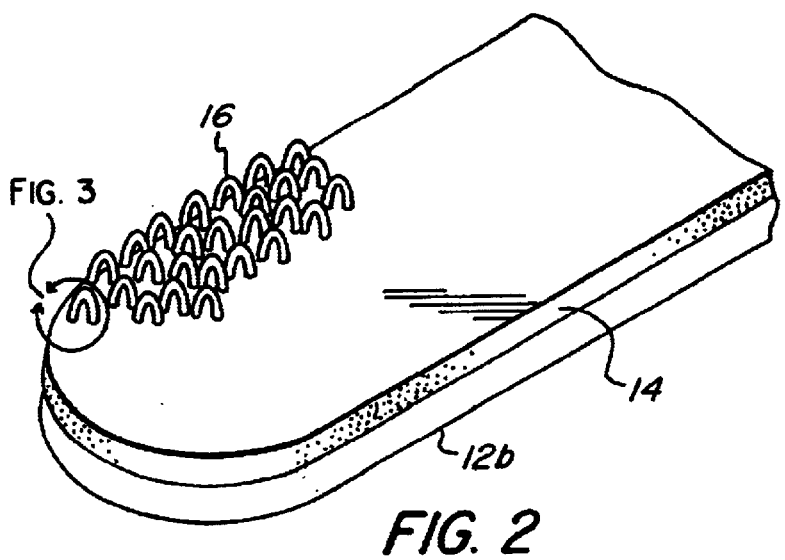
FIG. 2 is an enlarged, perspective view of a portion of the tongue cleaning device of FIG. 1.

Referring first to FIG. 1 a tongue cleaning device 10 in accordance with the present invention is shown. Tongue cleaning device 10 includes a flat, elongated member 12, which functions as both a handle 12a for gripping and as a head having a flattened portion or platform 12b. Attached to flattened portion 12b of elongated member 12 is a backing material 14 having a plurality of cleaning projections 16 protruding therefrom (as best seen in FIG. 2), which together comprise a cleaning portion 18. The backing material is coated on one side with an adhesive for attachment to the head 12b.

Figure 3:
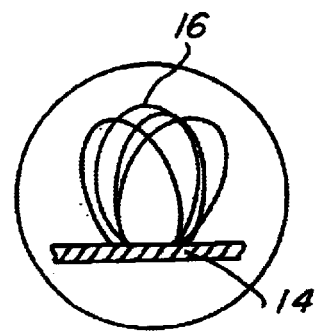
FIG. 3 is a further enlarged, perspective view of a portion of the tongue cleaning device of FIG. 2; and, FIG. 4 is a top view illustrating a preferred shape for a tongue cleaning device in accordance with the present invention.

The cleaning portion 18 is comprised of a plurality of projections 16 which extend outwardly with respect to the head 12b. The projections 16 may be made of a plurality of fiber loops such as those found on the loop side of Velcro® hook and loop fasteners. All projections 16, no matter what the style, are independently and individually movable. FIG. 3 illustrates in more detail projections 16 and backing material 14.

Elongated member 12, which functions as both a handle 12a for gripping and as a head having a flattened portion or platform 12b, is integrally formed of a flexible material, such as a thin, flexible plastic material. The head portion 12b has a periphery which is sized and shaped to fit within the roof of a user's mouth. The flexible nature of the head 12b allows the user to press the brush head 12b against the roof of the mouth to conform the head 12b to the shape thereof, while rubbing the tongue thereagainst. The flexible nature of the handle 12a allows the handle 12a to conform to the shape of the front teeth or gums in order to allow the head 12b to be pressed against the roof of the mouth without interference thereby.

In operation, the head 12a, with cleaning portion 18, is inserted into the mouth and is pressed against the roof thereof by the tongue. Due to the flexible nature of the head 12b and the handle 12a, the head 12b can be pressed with the tongue against the roof of the mouth to conform the head 12b to the shape thereof. The tongue is then rubbed against the cleaning portion 18 of the head 12a in any motion (i.e., back and forth, circular motions, etc.) which is comfortable for the user. As the surface of the tongue is moved along head 12a, the cleaning portion 18, and more specifically, the projections 16, remove the coating on the tongue including food particles and certain bacteria, and provides a deep cleansing of the entire topography, including pores, of the tongue. The projections 16 also act to trap debris removed from the tongue while, being soft and pliable, causing little or no irritation of the tongue. This cleaning action minimizes the potential for causing a gag reflex, as opposed to brushes which must be dragged over the surface of a protruding tongue.

Tongue cleaning device 10 may be used in conjunction with an antiseptic and/or antimicrobial compound in order to aid in disinfection of the tongue and mouth, which compound is carried in the cleaning portion 18. Tongue cleaning device 10 may be packaged with such compounds, or such compounds may be applied to tongue cleaning device before each use. One example of such a compound is Biotene® oral care preparation distributed by Laclede, Inc. of Rancho Dominguez, Calif. Biotenee is an antiseptic compound which kills germs with natural enzymes instead of alcohol, and also contains liquid calcium which may, over time, help to strengthen the user's teeth. However, it should be understood that substantially any mouthwash or oral antiseptic could be used with tongue cleaning device 10.

Once the user has performed an appropriate number of cleaning strokes on the upper surface of the tongue, the head 12a can be rinsed with hot water to remove the debris and prepare the device 10 for the next usage. If the surface of the tongue is excessively soiled, a rinsing operation may be performed once or more between cleaning strokes. The tongue cleaning device 10 can be used numerous times before deterioration of the cleaning portion 18 requires disposal of the apparatus 10. However, due to its simple design, tongue cleaning device 10 is inexpensive to manufacture, and therefore conducive to disposable use. As such, device 10 may simply be disposed of after a single use, thereby obviating the need for cleaning.

When tongue cleaning device 10 is packaged for single disposable use, it is particularly conducive to being packaged with an antiseptic and/or antimicrobial compound, as described above. This facilitates use and does not require the user to purchase such a compounds separately. Tongue cleaning device 10 may simply be packaged in individual plastic packages submerged in the antiseptic and/or antimicrobial compound. On the other hand, when tongue cleaning device 10 is packaged for multiple uses, where the user cleans device 10 between uses, it is particularly conducive to being packaged without an antiseptic and/or antimicrobial compound. Instead, the user may submerge the head 12a in the compound of his/her choice before each use. Of course, it should be understood that no antiseptic and/or antimicrobial compound is required, and tongue cleaning device 10 has significant benefits even without the use of such compounds.

Figure 4:
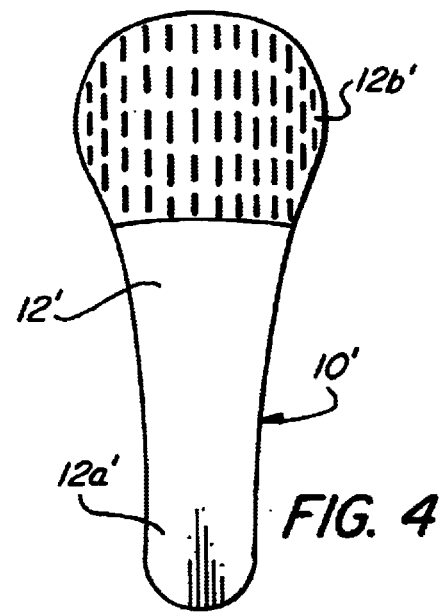

Elongated member 12, which functions as both a handle 12a for gripping and as a head having a flattened portion or platform 12b, may have any of numerous shapes. However, a particularly desirable embodiment is illustrated in FIG. 4. In this embodiment, tongue cleaning system 10' includes an elongated member 12' having a head 12b' which is wider than handle portion 12a'. This configuration facilitates deformation of handle 12a' around the front teeth or gums of the user, so as to allow the head 12b' to be pressed with the tongue against the roof of the mouth, while also allowing the head 12b' to be wide enough so that substantially the entire top surface of the tongue can be cleaned simultaneously. It has also been found that this configuration allows system 10 to be used by a number of users having varying mouth sizes.

The present invention, therefore, provides a tongue cleaning device which is relatively small and has a periphery which fits within the roof of a user's mouth, which is relatively simple in design and not costly to manufacture, and therefore conducive to disposable use, which may be used by a number of users having varying mouth sizes, which is flexible and can be contoured to the roof of the user's mouth, which can be contoured to the user's tongue during use, thus evenly distributing pressure across the tongue and promoting even cleaning at all desired tongue locations, and which avoids causing a user to gag during tongue cleaning.

Although the invention has been described with reference to a particular arrangement of parts, features and the like, these are not intended to exhaust all possible arrangements or features, and indeed many other modifications and variations will be ascertainable to those of skill in the art.

What is claimed is:

1. A tongue cleaning device adapted to be pressed against a top surface of a user's mouth, comprising:
   an elongated member integrally formed of a flexible material, said elongated member having a handle portion and a head portion;
   said head portion for contact with the top surface; and
   a cleaning portion comprising a first layer and second layer attached to the head portion of said elongated member, said first layer is said head portion of said elongated member and said second layer is backing material;
   said cleaning portion further comprising a plurality of cleaning projections protruding outwardly from said second layer;
   wherein said head portion of said elongated member is adapted to be pressed with the tongue against the top surface to conform the head portion to the shape thereof;
   wherein said handle portion is of a deformable material for deforming around a user's teeth; and
   wherein said head portion has a periphery which is sized and shaped to fit within the roof of a user's mouth.

2. The tongue cleaning device of claim 1 wherein said elongated member is integrally formed of a thin, flexible plastic material.

3. The tongue cleaning device of claim 1 wherein said cleaning portion comprises a backing material having an adhesive on a first surface thereof adhered to the head portion of said elongated member, and having a plurality of projections protruding from a second surface thereof.

4. The tongue cleaning device of claim 3 wherein the plurality of projections comprise a plurality of fiber loops.

5. The tongue cleaning device of claim 4 wherein the cleaning portion comprises a loop portion of a hook-and-loop fastening system.

6. The tongue cleaning device of claim 1 further comprising an antiseptic or antimicrobial compound carried in said cleaning portion.

7. The tongue cleaning device of claim 1 wherein the head portion of said elongated member is wider than the handle portion of said elongated member.

8. A tongue cleaning device adapted to be pressed against a top surface of a user's mouth, comprising:
   an elongated planar member integrally formed of a thin, flexible plastic material, said elongated member having a handle portion and a head portion;
   said head portion in contact with the top surface; and
   a cleaning portion comprising a backing material having an adhesive on a first surface thereof adhered to the head portion of said elongated member, and having a plurality of fiber loops protruding from a second surface thereof;
   wherein said head portion of said elongated member is pressed with the tongue against the top surface to conform the head portion to the shape thereof;
   wherein said handle portion is of a deformable material for deforming around a user's teeth; and
   wherein said head portion has a periphery which is sized and shaped to fit within the roof of a user's mouth.

9. The tongue cleaning device of claim 8 wherein the cleaning portion comprises a loop portion of a hook-and-loop fastening system.

10. The tongue cleaning device of claim 8 further comprising an antiseptic or antimicrobial compound carried in said cleaning portion.

11. The tongue cleaning device of claim 8 wherein the head portion of said elongated member is wider than the handle portion of said elongated member.

12. A tongue cleaning device adapted to be pressed against a top surface of a user's mouth, comprising:
   an elongated member integrally formed of a thin, flexible plastic material, said elongated member having a handle portion and a head portion, the head portion having a width greater than a width of the handle portion;
   said head portion for contact with the top surface; and
   a cleaning portion attached to the head portion of said elongated member, said cleaning portion comprising a backing material and a loop portion of a hook-and-loop fastening system; and
   an antiseptic or antimicrobial compound carried in said cleaning portion;
   wherein said head portion of said elongated member is adapted to be pressed with the tongue against the top surface to conform the head portion to the shape thereof;
   wherein said handle portion is of a deformable material for deforming around a user's teeth; and
   wherein said head portion has a periphery which is sized and shaped to fit within the roof of a user's mouth.

* * * * *